(12) United States Patent
Clements et al.

(10) Patent No.: US 6,391,598 B1
(45) Date of Patent: May 21, 2002

(54) PREPARATION OF FATTY ACID METAL SALTS AND ENZYMES FROM RUMINAL FLUID

(75) Inventors: L. Davis Clements; Ajoy Y. K. Koppolu, both of Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/538,852

(22) Filed: Mar. 28, 2000

Related U.S. Application Data (60) Provisional application No. 60/126,755, filed on Mar. 29, 1999.

(51) Int. Cl.$^7$ .............................. C12P 7/64; C12N 9/24; C12N 9/26
(52) U.S. Cl. ..................... 435/134; 435/200; 435/201
(58) Field of Search ................... 435/200, 134, 435/201

(56) References Cited

U.S. PATENT DOCUMENTS

| | | | |
|---|---|---|---|
| 445,055 A | 1/1891 | Giebermann | 71/15 |
| 2,171,198 A | 8/1939 | Urban et al. | 554/178 |
| 2,261,923 A | 11/1941 | Pittman et al. | 530/420 |
| 3,738,933 A | 6/1973 | Hollo et al. | 210/804 |
| 4,578,352 A | * 3/1986 | Katkocin et al. | 435/99 |
| 4,606,836 A | * 8/1986 | Gancy | 252/70 |
| 4,629,785 A | 12/1986 | McLaffery, III | 530/415 |
| 4,675,114 A | 6/1987 | Zagyuia et al. | 210/666 |
| 4,765,908 A | 8/1988 | Monick et al. | 210/666 |

OTHER PUBLICATIONS

Leuschner, Energy Res. Abstr., 1989, 14(9), Abstr. No. 17677.*

"The Rumen and its Microbes", Hungate, Academic Press, 1966, pp. 84, 85, 192–199, 296–299.*

"Ph Dependence of Carboxylic and Mineral Acid Extraction by Amine–based Extractants: Effects of pKa, Amine Basicity, and Diluent Properties", Eyal and Canari, Ind. Engng. Chem. Res. 34:5 1789–1798 (1995).

"Surface Diffusion Kenetics in the Adsorbtion of Acetic Acid on Activated Carbon", Ganguly and Goswami, Sep. Sci. Tech. 31:9 1267–1278, (1996).

"Recovery and Separation of Mixtures of Organic Acids from Dilute Aqueous Solutions", Shama and Jagirdar, J. Sep. Proc. Technol., 1:2 40–43, (1980).

"Extraction of Carboxylic Acids With Tertiary and Quaternary Amines: Effect of pH", Yang et al., Ind. Engng. Chem. Res. 10:6 1335–1362, (1991).

"Coupling Ion Pair Extraction With Adsorbtion for the Separation of Acidic Solutions for Water", Payne and Ramarkrishnan, Ind. Eng. Chem. Res., (1995).

"Purification of Industrial Alpha–amylase by Reversed Micellar Extraction", Chang and ChenBiotech, Bioengng, 48, 745–748, (1995).

"Extraction and Sorbtion of Acetic Acid at pH Above pKa to form Calcium Magnesium Acetate", Reisinger and King, Ind. Sep. Proc. Technol., 34, 845–852, (1995).

"Measurement of Cellulase Activities", Ghose, Pure Appl. Chem, 59:2 257–268, (1987).

* cited by examiner

*Primary Examiner*—David M. Naff
*Assistant Examiner*—Mike Meller
(74) *Attorney, Agent, or Firm*—James D. Welch (57) ABSTRACT

A method for producing at least one metal salt of a fatty acid is disclosed. The process first obtains from animal rumen, ruminal fluid containing at least one fatty acid. Next, at least one metal oxide is added to the ruminal fluid. One metal salt of a fatty acid is formed from the addition of these two components. Lastly, the process involves recovering at least some of the at least one metal salt of a fatty acid. The ruminal fluid also contains enzymes which are isolated in the process.

12 Claims, 7 Drawing Sheets

PREPARATION OF FATTY ACID METAL SALTS AND ENZYMES FROM RUMINAL FLUID

This Application is a CIP of Provisional Application Ser. No. 60/126,755, filed Mar. 29, 1999.

TECHNICAL FIELD

The present invention relates to methods of recovering valuable components present in waste streams and effluents from anaerobic digestion systems, and more particularly comprises a partitioning method for recovering salts of volatile fatty acids, as well as undenatured enzymes in valuable forms.

BACKGROUND

The coexistence of small organic species, like acids and alcohols, with protein molecules is a common occurrence in various processing streams. For example, fermentation broths usually contain acids, vitamins and enzymes and are formed in conjunction with the manufacture of some industrially important proteins or in the cultivation of bacteria or fungi as extracellular components. Similar materials are found in the sera of animals and humans and as effluents in waste streams from meat processing streams, as well as in anaerobic digester effluents, (eg. from cattle rumens for instance), and all said examples present industry with a continuing disposal problem.

Further, it is known that said waste streams and anaerobic digester effluents typically contain components including valeric, acetic, propionic and butryic volatile fatty acids, and enzymes such as alpha-amylase and cellulase, as well as other proteins, many of which components are valuable and can be sold if available in separated-out, usable, form. And, as an added benefit, where such components are separated-out of waste streams or anaerobic digestion system effluents, the remaining waste or effluent can be easier to process to the point it can be disposed of, as the BOD requirement is often reduced.

As well, regarding waste streams or effluents such as are developed in meat processing plants, the recovery of useful chemicals therefrom, or their complete treatment is often mandated by local or federal regulations, (eg. where acetic and other carboxylic acids are present in the waste materials).

Beneficially, separation of valuable acids and/or enzymes can convert a waste stream into a value added stream and thereby create positive cash flow where otherwise disposal costs are required.

With the foregoing in mind, it is noted that adsorption combined with extraction, has long been the method of choice when other conventional separation methods prove too expensive and/or are energy intensive.

As described by Eyal and Canari in an article titled "Ph Dependence of Carboxylic and Mineral Acid Extraction by Amine-based Extractants: Effects of pKa, Amine Basicity, and Diluent Properties", Ind. Engng. Chem. Res. 34:5 1789–1798 (1995); and by Ganguly and Goswami in an article titled "Surface Diffusion Kenetics in the Adsorbtion of Acetic Acid on Activated Carbon", Sep. Sci. Tech. 31:9 1267–1278, (1996); adsorption and extraction are commonly used methods for the separation of acids from dilute streams.

Low molecular weight aliphatic carboxylic acids appear in many industrial and effluent streams and the recovery thereof by solvent extraction, with or without reaction, has been studied by Shama and Jagirdar and reported in an articel titled "Recovery and Separation of Mixtures of Organic Acids from Dilute Aqueous Solutions", J. Sep. Proc. Technol., 1:2 40–43, (1980).

Amine-based extractants, because of their effectiveness and selectivity, are favored over other extractants in the recovery of acids from aqueous solutions as reported in an article titled "Extraction of Carboxylic Acids With Tertiary and Quaternary Amines: Effect of pH", Yang et al., Ind. Engng. Chem. Res. 10:6 1335–1362, (1991).

Partitioning studies of various organic compounds using both adsorbents and extractants have also been documented by King in an article titled "Acid-base Equilibria" in the encyclopedia of Physical Chemistry and Chemical Physics, Pergamon Press, Oxford (1965); and in an article titled "Coupling Ion Pair Extraction With Adsorbtion for the Separation of Acidic Solutions for Water", Payne and Ramarkrishnan, Ind. Eng. Chem. Res., (1995).

Adsorbents are generally employed in separations using column liquid chromatography for proteins and other organic solutes. Adsorption of molecules of different sizes and surface charges has been investigated by Tien in an article titled "Adsorbtion Calculations and Modeling", Butterworth-Heinemann, Mass. (1994).

Recently amine-based experiments to extract and recover alpha-amylase from reverse micellar solutions has been reported by Chang and Chen titled "Purification of Industrial Alpha-amylase by Reversed Micellar Extraction", Biotech, Bioengng, 48, 745–748, (1995).

It is noted that a use for salts of (APB's) is as de-icers as discussed in an article titled "Chemical Deicers and the Environment", D'Itrl, Lewis Publishers, Mich., (1992).

Further, commonly utilized de-icers are more corrosive than are esters, such as an acetate, as reported by Reisinger and King in an article titled "Extraction and Sorbtion of Acetic Acid at pH Above pKa to form Calcium Magnesium Acetate", Ind. Sep. Proc. Technol., 34, 845–352, (1995), hence use of metal esters such as CaMg Acetate, CaMg Propionate etc. can be projected as providing environmentally friendly results.

It is specifically noted that for any dilute aqueous stream which contains acids and enzymes, the operating parameters for separating out the acids are different than those for recovering the enzymes and importantly, successful simultaneous separation of both acids and proteins has not before been reported. The present invention, however, teaches that uptake of carboxylic acids and enzymes, alpha-amylase and cellulase from solution can be achieved, where the enzymes are preferentially sequestered, either by leaving the acids in solution or by partitioning the acids into a different phase. And, since unlike solutes do not compete simultaneously with the non-aqueous phase (organic or solid), high percentage separations for acids and enzymes can be achieved.

Present invention experimental work has focused on acetic, propionic and butyric acids and protein compounds including alpha-amylase arid cellulase, (which enzymes are industrially important in degradation of starch and cellulose, respectively), but the approach of using an organic extractant and solid adsorbent to simultaneously separate acids and enzymes is applicable to other systems.

The principal advantage of using organic extractant and solid adsorbent to simultaneously separate acids and enzymes is the ease with which these phases can be separated from an aqueous phase. The extractant and solid phases can be separated from the aqueous phase and the respective phases can be stripped of solutes, allowing the process to be made continuous.

If one solute shows a distinct affinity towards an adsorbent/extractant in the presence of other solutes, then it can be recovered initially.

A Search of Patents has provided a Patent to Monick et al., U.S. Pat. No. 4,765,908 which describes a process and composition for removing contaminants from wastewater. Many chemical compositions are identified for removing heavy metals such as Sodium and Calcium Bentonite, Montmorillonite, calcium carbonate, calcium oxide, calcium hydroxide, lime, aluminum sulfate and a catalist, zirconium. Recovery of enzymes is not a focus.

U.S. Pat. No. 4,675,114 to Zagyvai et al., describes a process for dewatering sludges containing proteinic organic contaminates and for separating solid particles from the aqueous phases. The use of calcium hydroxide and/or magnesium oxide to produce an alkaline sludge pH is mentioned. The use of formaldehyde is described and the methodology does not focus on sequential removal of enzymes followed by removal of other elements.

U.S. Pat. No. 4,629,785 to McCaffery, III, describes a procedure in which proteinaceous material is separated from cationic species by an adsorption process. Converting active microorganisms to inactive form is disclosed.

U.S. Pat. No. 2,171,198 to Urbain et al., describes use of Zinc Oxide to remove and recover fatty acids from waste.

U.S. Pat. No. , 3,738,933 to Hollo et al., describes a process for recovering protein from sewage which uses bentonite or kaolin in combination with a calcium compound such as lime milk or calcium hydroxide, aluminum, bi and tri-valent iron.

U.S. Pat. No. 445,055 to Giebermann describes the use of alumina to sequester gluten in slaughter house washings.

U.S. Pat. No. 2,261,923 to Pittman describes use of bentonite to sequester protein from distillery slop.

No known prior teachings, however, provide for partitioning of acids and enzymes into different phases to allow separate undenaturing processing thereof, while leaving unpartitioned solutes in an aqueous phase.

A need is thus identified for economical, easy to practice, methods for separating-out volatile fatty acids, enzyme and possibly other protein components from waste streams and anaerobic digester effluents, and providing said separated-out components are in forms which have economical value.

DISCLOSURE OF THE INVENTION

The present invention provides at least three specifically identifiable modifications of a procedure, the practice of which results in separation of, at least, volatile fatty acids in a valuable salt form which can be, for instance, used as a de-icer. In addition, the present invention procedure can also provide enzymes, (eg. in particular alpha-amylase and cellulose), in undenatured, separated-out form.

The First variation of the present invention can be recited as a method of providing "paunchate" comprising salts of volatile fatty acids comprising, in any functional order, the steps of:

a. providing a waste stream or anaerobic digester system effluent which comprises volatile fatty acids typically including acetic and/or propionic and/or butyric acids, as well as proteins and/or enzymes typically including alpha-amylase and/or cellulase;

b. optionally separating-out particulate solids therefrom;

c. mixing oxides comprised of at least one selection from the group consisting of: (any Group IIA and Group IIB Metal Oxide), into the solution resulting from practicing step a. and optionally step b., such that "paunchate" comprising volatile fatty acid salts is provided in a separated-out form.

The Second variation of the present invention can be recited as a method of separately providing:

enzyme(s) typically including alpha-amylase; and

"paunchate" comprising salts of volatile fatty acids;

comprising, in any functional order, the steps of:

a. providing a waste stream or anaerobic digester system effluent which comprises a solution of volatile fatty acids including acetic and/or propionic and/or butyric acids, as well as proteins and/or enzymes tyically including alpha-amylase and/or cellulose;

b. optionally separating-out particulate solids therefrom;

c. subjecting the solution resulting from practicing step a. and optionally step b. to enzyme adsorption, and optionally desorption, such that at least alpha-amylase is provided in undenatured separated-out of solution form;

followed by:

d. mixing oxides comprised of at least one selection from the group consisting of: (any Group IIA and Group II Metal Oxide), into the remaining solution resulting from practice of step c., such that "paunchate" comprising volatile fatty acid salts is provided in a separated-out form.

The Third variation of the present invention can be recited as a method of separately providing:

enzymes, typically including alpha-amylase; and

"paunchate", typically comprising salts of volatile fatty acids;

comprising, in any functional order, the steps of:

a. providing a waste stream or anaerobic digester system effluent which typically comprises a solution of volatile fatty acids including, typically, acetic and/or propionic and/or butyric acids, as well as, typically, proteins and/or enzymes typically including alpha-amylase and cellulase;

b. optionally separating-out particulate solids therefrom;

c. treating the solution resulting from practicing step a. and optionally step b. to organic enzyme extractant in the presence of a selection from the group consisting of: (bentonite and functional equivalents thereto), such that adsorption of at least alpha-amylase onto said selection from the group consisting of: (bentonite and functional equivalents thereto) occurs, optionally followed by causing desorption of said alpha-amylase from said selection from the group consisting of: (bentonite and functional equivalents thereto), such that at least said alpha-amylase is provided in an undenatured separated-out of solution form;

said method further comprising:

d. mixing oxides comprised of at least one selection from the group consisting of: (any Group IIA and Group IIB Metal Oxide), into the remaining solution resulting from practice of step c., such that "paunchate" comprising volatile fatty acid salts is provided in a separated-out form, accompanied by recovery of said organic enzyme extractant.

In any of the foregoing examples, the "paunchate" resulting from the practice thereof can consist of selection(s) from the group consisting of:

calcium-valerate;

calcium-acetate;

calcium-propionate;

calcium-butyrate;

calcium-magnesium-acetate;

calcium-magnesium-propionate; and calcium-magnesium-butyrate.

Further, in any of the foregoing examples, the separation of cellulase can also be performed, with a preferred approach thereto being by a size exclusion chromatography procedure.

It is also noted that any of said methods can provide a solution remaining after practice of the last step therein which has a reduced BOD as compared to the original waste stream or anaerobic digester system effluent as provided in step a.

It is further noted that the volatile fatty acid salt "paunchate" produced by any of the above methods is suitable for use as deicer.

The invention will be better understood by reference to the Detailed Description Section of this Specification, in conjunction with the Drawings.

SUMMARY

It is therefore a primary purpose and/or objective of the present invention to provide economical, easy to practice, methodology for separating-out volatile fatty acids, enzyme and possibly other protein components from waste streams and anaerobic digester effluents, and providing said separated-out components in forms which have economical value.

It is another purpose and/or objective of the present invention to provide systems for practicing the methodology.

Other purposes and/or objectives of the present invention will become clear from a reading of the Specification.

BRIEF DESCRIPTION OF THE DRAWINGS

FIG. 8a shows partition isotherms for acetic acid in the presence of sodium acetate, and for sodium butyrate, are similar.

DETAILED DESCRIPTION

Figure 1:
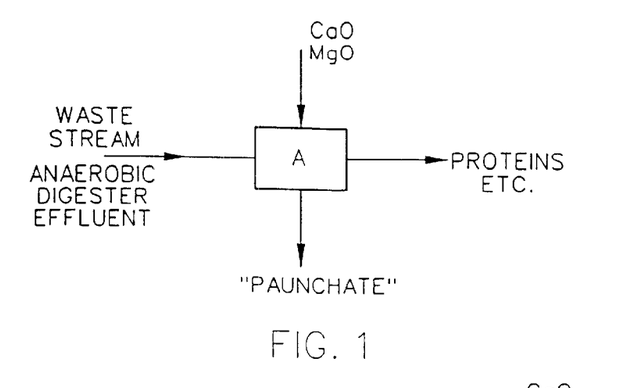
FIG. 1 shows a system for practicing a present invention Method.

A system for practicing the First present invention Method as disclosed in the Disclosure of the Invention Section herein, can be appreciated by referral to FIG. 1. FIG. 1 shows a waste stream or effluent from an anaerobic digester system being entered to a vessel (A) in which exemplary ZnO, CaO and or MgO is/are also entered, such that therein is formed, in a separated-out form, salts of volatile fatty acids, (ie. "paunchate"). It is noted that CaO/MgO is preferred but that many oxides can be utilized.

Figure 2:
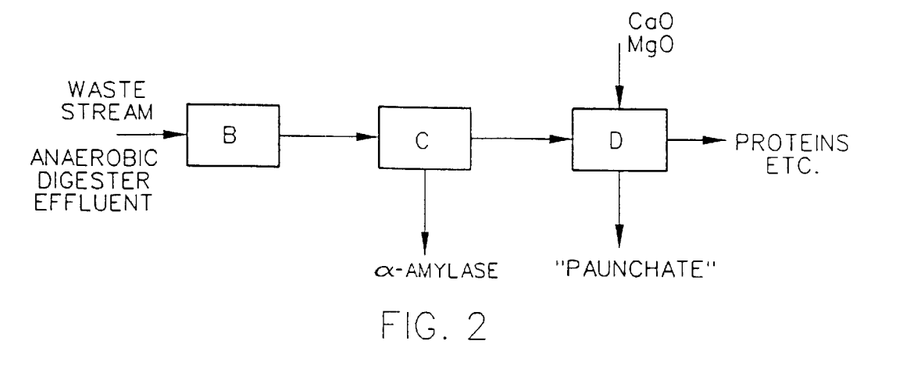
FIG. 2 shows a system for practicing a present invention Method.

A system for practicing the Second present invention Method as disclosed in the Disclosure of the Invention Section herein, can be appreciated by referral to FIG. 2. FIG. 2 shows a waste stream or effluent from an anaerobic digester system being entered to a vessel (B), in which vessel (B) is present an adsorbant which adsorbs enzymes (eg. alpha-amylase). The results obtained in vessel (B) are subjected to desorption in vessel (C) to provide separated-out alpha-amylase. The remaining mixture sent to vessel (D) wherein exemplary ZnO, CaO and or MgO is/are also entered, such that therein is formed in a separate form salts of volatile fatty acids (ie "paunchate"). It is noted that CaO/MgO is preferred but that many oxides can be utilized.

Figure 3:
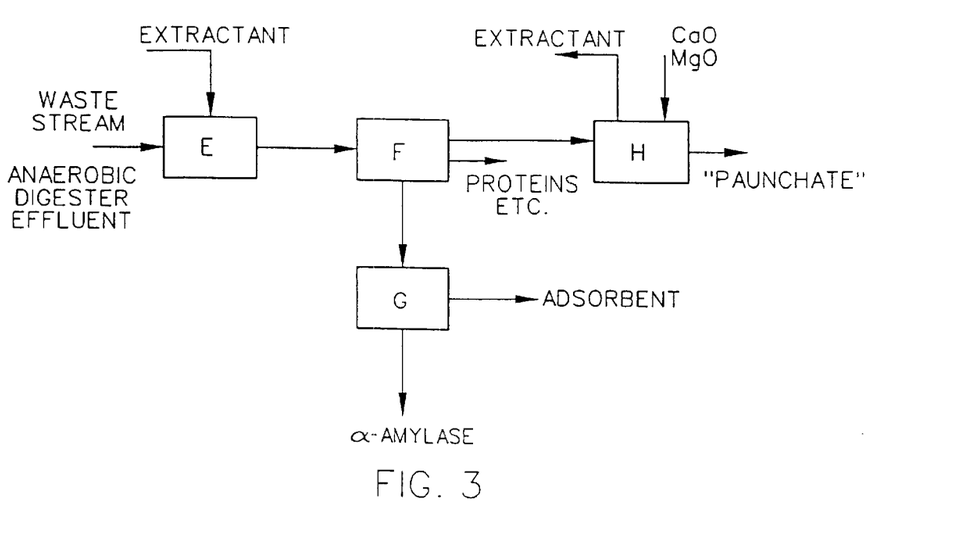
FIG. 3 shows a system for practicing a present invention Method.

A system for practicing the Third present invention Method as disclosed in the Disclosure of the Invention Section herein, can be appreciated by referral to FIG. 3. FIG. 3 shows a waste stream or effluent from an anaerobic digester system being entered to a vessel (E) along with an organic extractant, in which vessel (B) is present an adsorbant which adsorbs enzymes (eg. alpha-amylase). The results obtained in vessel (B) are sent to vessel (F), (note that vessels (E) and (F) can be a single, combined function unit), and are subjected to desorption in follow-on vessel (C) to provide separated-out alpha-amylase, and adsorbant. The remaining mixture sent to vessel (H) wherein exemplary CaO and or MgO is/are also entered, such that therein is formed in a separate form salts of volatile fatty acids (ie "paunchate"). Also indicated is recovery of the extractant originally entered to vessel (E). It is noted that CaO/MgO is preferred but that many oxides can be utilized.

Figure 4A:
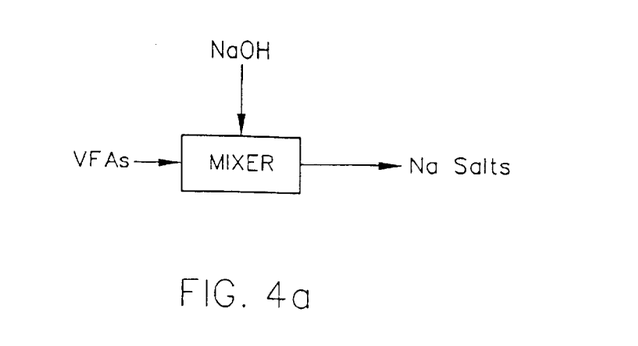
FIGS. 4a, 4b and 4c show additional possible present invention system configurations.
Figure 4B:
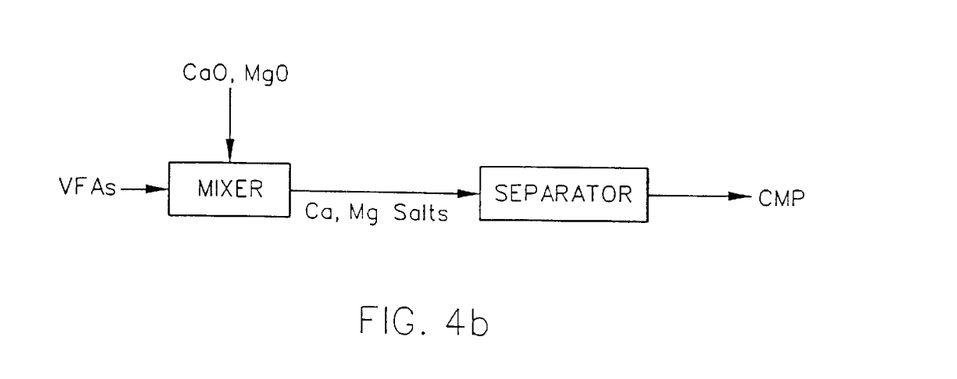
Figure 4C:
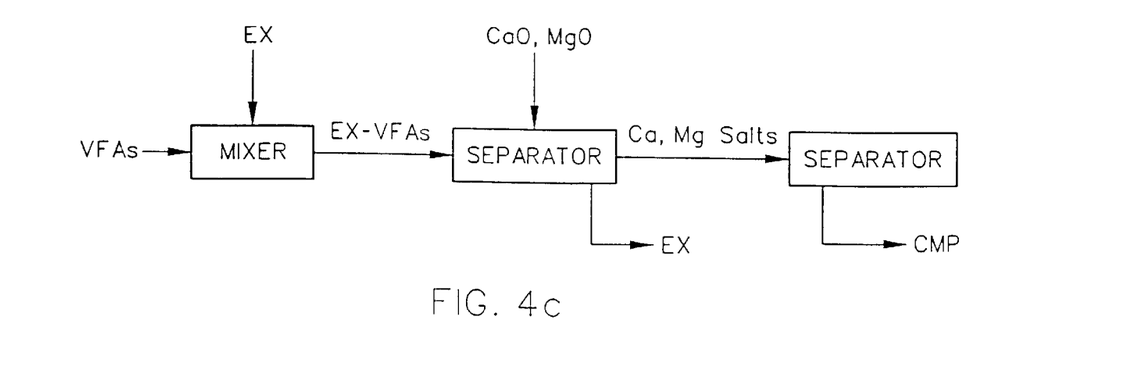

FIGS. 4a, 4b and 4c show additional possible present invention system configurations.

FIG. 4a shows sodium salts can be formed from the reaction of volatile fatty acids (VFA's) with sodium hydroxide. The carboxylates thus formed are very soluble in water and the literature reports therapeutic usage for these salts as described in U.S. Pat. No. 5,563,173 to see Yatsu and Ranganna (1996) as anti-proliferative agents. The salt solubility decreases for oxides of calcium, magnesium and zinc.

FIG. 4b shows a system including a separator for use in manufacturing calcium-magnesium acetate.

FIG. 4c shows a system which allows addition of an extractant in a different route to produce salts of acetic, propionic and butyric acids, (ie. APB's). With the addition of an organic extractant, such as an amine, the acids can be quantitatively complexed into an organic phase. Later the organic phase can be stripped to recover the carboxylic acids and the extractant. Following the stripping step, the metal oxides can be added to complete the reaction and provide Calcium-Magnesium-Paunchate (CMP).

EXAMPLES

With the preceding focused presentation in mind, attention is now turned to providing additional detail and insight to the basis of the present invention. The first example involves use of high purity (99+%) calcium, magnesium and zinc oxides (purchased from Mallinckrodt), a Spectronic 20D system was utilized to measure adsorbance for enzymatic assays. Rumen samples from grain-fed fistulated cows were collected one hour after feeding. The samples were filtered through cheese cloth and then centrifuged at 3000 g for 30 minutes to separate any remaining particulate matter. For gas chromatographic analyses, samples were further centrifuged at 20,000 g for 10 minutes and filtered through a 0.45 micron filter to remove any micro-particles. In the case of model solutions, acetic, propionic and butyric acids, (APB's), were mixed in the ratio of 60:25:15, respectively, to provide a final concentration of 10 gm/liter, (which is approximately the same as found in ruminal fluid concentrations). The experimental technique provided that total acid and individual contents of volatile fatty acids were determined by titration with NaOH and by gas chromatography for both model and ruminal samples. Amounts of oxides equal to or greater than those needed stoichiometrically were used for precipitating the carboxylic acids.

Assays for enzymatic activity were measured before and after the precipitation. Regarding alpha-amylase, activity was assayed using p-nitrophenyl maltoheptaoside as the substrate with p-nitrophenol as the reaction product. This technique is discussed in an article titled "Ethylidene Protected Substrate for the Assay of Human Alpha-Amylase", J. Anal. Chem., 324, 304–308, by Rauscher et al. (1986).

Cellulase activity was determined by the filter paper assay method, which gives reducing sugar as the final product. This technique is discussed by Ghose in an article titled "Measurement of Cellulase Activities", Pure Appl. Chem, 59:2 257–268, (1987).

It is noted that One International Unit of (IU) amylase and/or cellulase is defined as the amount of enzyme required to release one micro-mole of product per minute, and final activity was expressed in concentration units of International Units per Liter (IU/l).

Equations which describe the reactions, in the case of CaO, are:

$$CaO + 2HAc \rightarrow Ca(Ac)_2 + H_2O \quad\quad 1$$

$$CaO + H_2O \rightarrow Ca(OH)_2 \quad\quad 2$$

$$Ca(OH)_2 + 2HAc \rightarrow Ca(Ac)_2 + 2H_2O \quad\quad 3$$

$$HAc \rightleftharpoons H^+ + Ac^- \quad\quad 4$$

$$Ca(Ac)_2 \rightleftharpoons Ca^{2+} 2Ac^{31} \quad\quad 5$$

and similar equations apply in the case of Mg, and Zn.

Experiments on both model solution and ruminal fluids determined that acetic, propionic and butyric acid precipitation was best achieved using CaO. When MgO was used, results were not as good, but were better than when ZnO was utilized. Equimolar amounts were used to salt out. Combinations of oxides were also tested, and the results of the experiments are reported in Table 1.

TABLE 1

| Oxide used | Conversion | |
|---|---|---|
| | Model solutions | Rumen VFA |
| CaO | 97 | 70 |
| MgO | 88 | 63 |
| ZnO | 55 | 41 |
| CaO + MgO | 99 | 90 |
| CaO + ZnO | 95 | 85 |
| MgO + ZnO | 90 | 85 |

It is obvious that precipitation was improved when CaO/MgO pairs were used.

Figure 5:
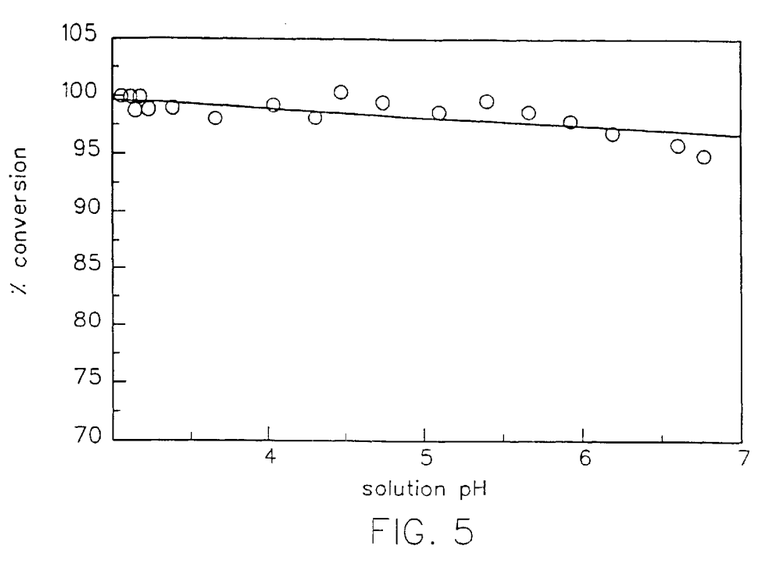
FIG. 5 shows the effect of the pH of a solution on the conversion of acetic, propionic and butyric acids, (APB's) into salts.

Further, FIG. 5 shows the effect of the pH of a solution on the conversion of acetic, propionic and butyric acids, (APB's) into salts. At less than 100% conversion, mainly at higher pH's, the solutions contain unreacted oxide and hydroxide.

Figure 6:
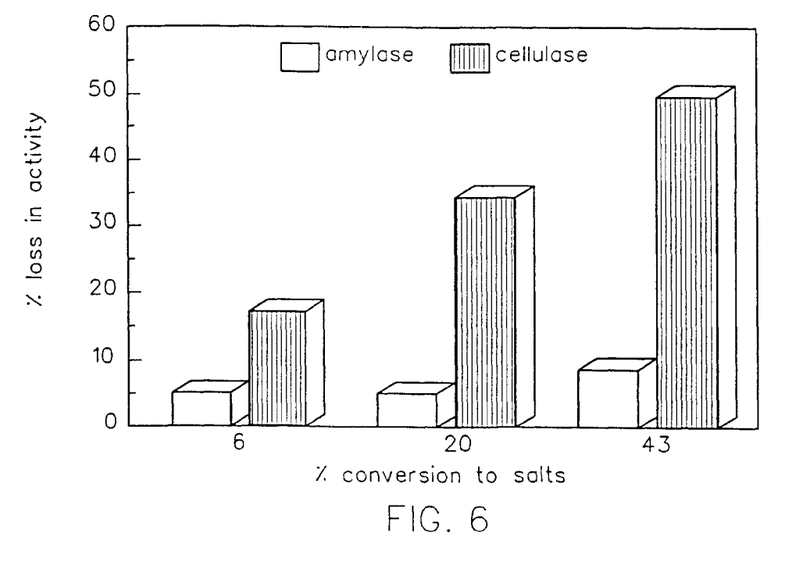
FIG. 6 shows that alpha-amylase activity was retained up to about 50% conversion of APB's into salts, while cellulase activity as lost even at very low conversions.

Additional experimentation was conducted with ruminal fluid to determine if the presence of CaO adversely affected enzyme activity. FIG. 6 shows that alpha-amylase activity was retained up to about 50% conversion of APB's into salts, while cellulose activity was lost even at very low conversions. Thus, precipitation of volatile fatty acids (VFA's) might be feasible where alpha-amylase is to be simultaneously recovered, but not where cellulase is to be recovered. It is thus greatly preferable to separate protein/enzymes from ruminal solution, prior to precipitation of VFA's therefrom, if enzyme activity is to be preserved.

From the preceding, it can be concluded that oxides of calcium, magnesium and zinc convert carboxylic acids into their salts, with calcium oxide CaO being preferred. However, the use of a CaO/MgO oxide pair provides additional utility in conversion of ruminal fluids VFA's into salts, which salts show promise as environmentally friendly de-icing agents. Further, it can be concluded that where enzymes are to be recovered in an active form, separation thereof prior to VFA precipitation is preferable.

The present invention further documents simultaneous separation of volatile fatty acids and enzymes from dilute aqueous streams coupling adsorption and extraction. It has already been demonstrated herein that separation of enzymes, from a waste stream or ruminal fluid, is necessary to preserve enzymatic activity where precipitation of volatile fatty acids present therewith, as their salts, is to be performed. Thus the present invention is further reported as comprising acid extraction using Alamine 336, coupled with adsorption of enzymes onto Bentonite. This approach provides three distinct phases which are easily separated by centrifugation. Acids are found primarily in an organic phase, while most alpha-amylase is found in an aqueous phase. Cellulase shows a high affinity for the adsorbent and is found primarily in a solid phase. It was also noted that salt ions coexistent with acidic solutions affect the extraction of single acids or mixtures of acids as a result of a combination of chain lengths and the nature of the salt ions in solution.

Results reported in the following were achieved using acidic solutes of an analytical grade obtained from Sigma. Alamine 336 was obtained from Henkel Corporation. A 1:1 volume ratio of aqueous to organic phase was used throughout the study and the acid concentration for either single or multiple solutes was kept below 100 mM. The alpha-amylase source was B. Licheniformis and that of cellulase from T. Viride, both acquired from Sigma. As mentioned before, alpha-amylase activity was assayed using p-nitrophenyl maltohepaoside as substrate as described in the previously cited article by Rauscher et al. (1986)

The cellulase activity was determined by the filter paper assay method which gives reducing sugar as the final product as described in the previously cited article by Ghose (1987).

And again, one International unit of amylase and cellulase is defined as the amount of enzyme required to release one micromole of product per minute. The final activities were expressed in concentration units as IU/Liter.

Acids were quantified by titration and also by gas chromatography. A HP 6890 GC, equipped with a FID, capillary inlet system and GC protector was used throughout the analysis. The chromatograph was controlled and interfaced to a HP Vectra PC and the HP 3365 ChemStation quantitative analysis and report making software. The separation was carried out with a 0.25 mm ID×30 m×0.25 micron HP-Innowax capillary column bonded with a cross-linked polyethylene glycol. Helium was used as the carrier gas. Sample solution (ca. 1.0 microliter) was loaded into the injection port at 280 degrees Centigrade with a split ration of 1:40 with an electronic pressure control. The inlet pressure of the carrier gas was controlled at 24 psi and the linear velocity was 42 cm/sec at the initial column-oven temperature of 120 degrees Centigrade. The initial oven temperature was held for 1 minute and then programmed up to 265 degrees Centigrade at 10 degrees Centigrade/ minute and held for 2 minutes at the final temperature. The eluent was detected with a FID at 300 degrees Centigrade.

Sorbtion studies of enzymes with bentonite were carried out at different pH's to see the optimal uptake from solution without acidic solutes. The amount of bentonite used in the experiments was fixed at 4 gm/liter, the capacity at which the percentage adsorption was at least 90. The concentration range for alpha-amylase was from 100 to 500 IU/Liter and that of cellulase from 15 to 75 IU/Liter. Cellulase showed good adsorptivity onto bentonite and other adsorbents tested were also effective. But, its desorptivity was very poor. By contrast, alpha-amylase was able to desorb by either changing the pH or the ionic strength of the solution. Also, the carboxylic acids showed little or no affinity towards bentonite, (less than 2% of the total acid taken was adsorbed), but were adsorbed to varying extents with other adsorbents.

Table 2 shows the behavior of alpha-amylase adsorption onto bentonite with varying pH at two different ionic strengths. The uptake of alpha-amylase is a strong function of pH and decreases beyond neutral pH, and also below its isoelectric point. Acids and their corresponding salts affect the ionic strength of solution. As also shown in Table 2, the influence of ionic strength as compared to pH is small and adsorption variations caused in ionic strength can be neglected for the range of acid concentration examined.

TABLE 2

| I = 50 mM | | I = 100 mM | |
|---|---|---|---|
| pH | % adsorbed | pH | % adsorbed |
| 5.25 | 88 | 5.35 | 88 |
| 5.65 | 100 | 5.62 | 94 |
| 6.0 | 97 | 5.95 | 97 |
| 6.28 | 94 | 6.2 | 87 |
| 6.67 | 86 | 6.45 | 80 |
| 6.92 | 80 | 6.95 | 72 |

Figure 7:
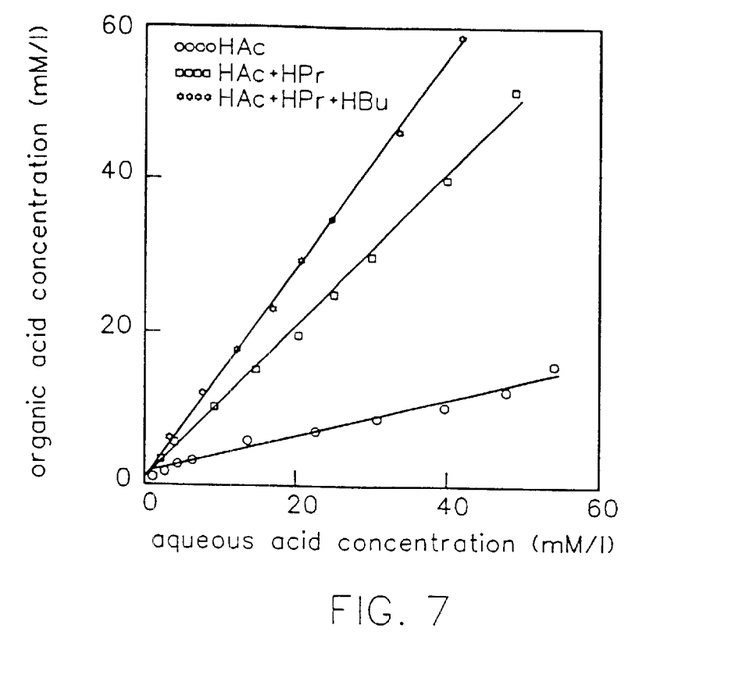
FIG. 7 shows partition isotherms for three different volatile fatty acid cases.
Figure 8A:
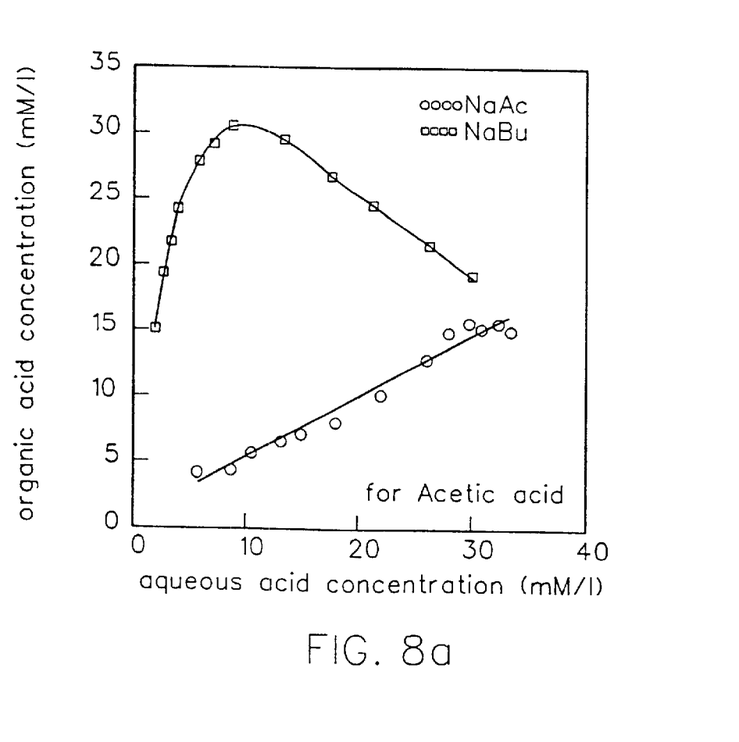
Figure 8B:
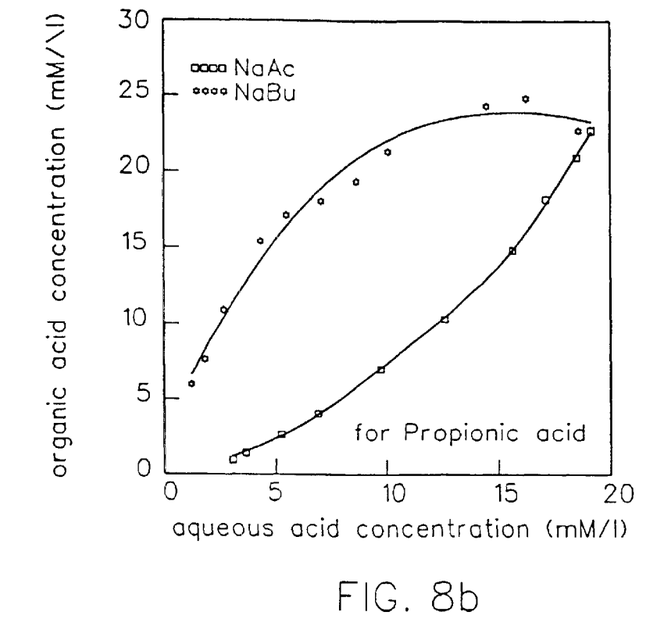
FIGS. 8b and 8c shows partition isotherms for propionic and butyric acids, respectively.
Figure 8C:
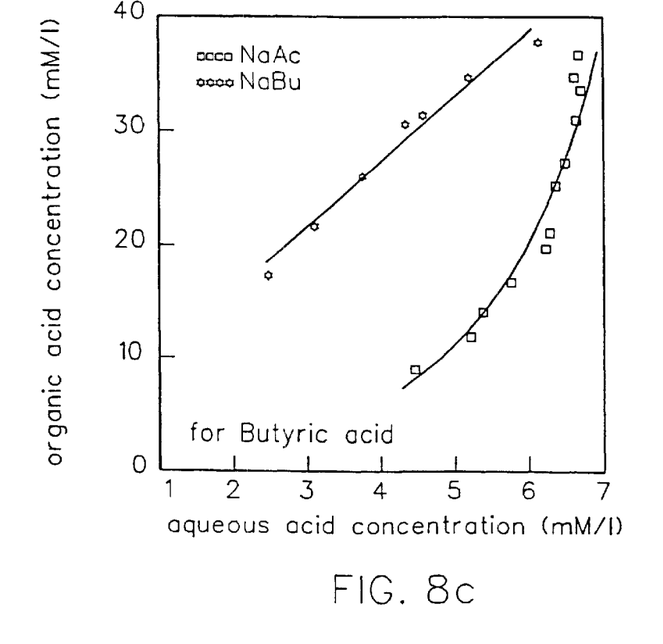

As regards the separation of acids, FIG. 7 shows partition isotherms for three different cases. The equilibrium acid concentration in the organic phase increases linearly with aqueous phase acid concentration. Also, the distribution of acids into the amine phase increases as the chain length or hydrophobicity of the acids increases. It is also evident from FIG. 7 that the slopes or distribution coefficients are constant. If the system were ideal, the extraction mechanism of an acid can be expressed as:

$$Ha_a \leftrightharpoons HA_o \qquad 6$$

$$R_3N{:}_o + HA_o \leftrightharpoons R_3N{:}HA_o \qquad 7$$

$$K_p = [HA]_o/[HA]_a \qquad 8$$

$$K_{s1} = [R_3N{:}HA]_o/\{[R_3N{:}]_o[HA]_o\} \qquad 9$$

where $K_p$ is the partition coefficient and $K_{s1}$ is the equilibrium constant for Equation 9, and where subscripts a and o refer to aqueous and organic phases. The results in FIG. 7 suggest that $K_p$ is constant for the range of acid concentrations investigated. This, however, is rarely the case. The acidic solutes are to some degree found in neutralized form and therefore, the simultaneous occurrence of their salts is not uncommon. As shown in FIG. 8a, the partition isotherms for acetic acid in the presence of sodium acetate and sodium butyrate are similar. The extraction mechanism for acetic acid with sodium acetate in solution is not different from the case presented in FIG. 7. Therefore the partition coefficient, $K_p$ is still constant. But, when the salt species is sodium butyrate the isotherm is no longer linear, suggesting a dependence of partition coefficient on salt concentration. The equations that should be given to include the effect of salt ions are:

$$R_3N{:}HA_o + B^-_a \leftrightharpoons R_3N{:}HB_o + A^-_a \qquad 10$$

where $$K_{s2} = [R_3N{:}HB]_o[A^-]_a/\{[R_3N{:}HA]_o[B^-]_a\} \qquad 11$$

describes the equilibrium relationship for the exchange of the long chain salt ion for the low molecular weight ion. A similar result is depicted in FIGS. 8b and 8c for propionic and butyric acids. The non-linearity of the partition coefficient also suggests that the formation of diners in the organic phase with low dielectric strength is also a possibility:

$$Ha_o \leftrightharpoons (HA)_{2o} \qquad 12$$

and $$K_{s3} = [(HA)_2]_o/[HA]^2_o \qquad 13$$

as described in a previously cited article by King (1965).

Figure 9A:
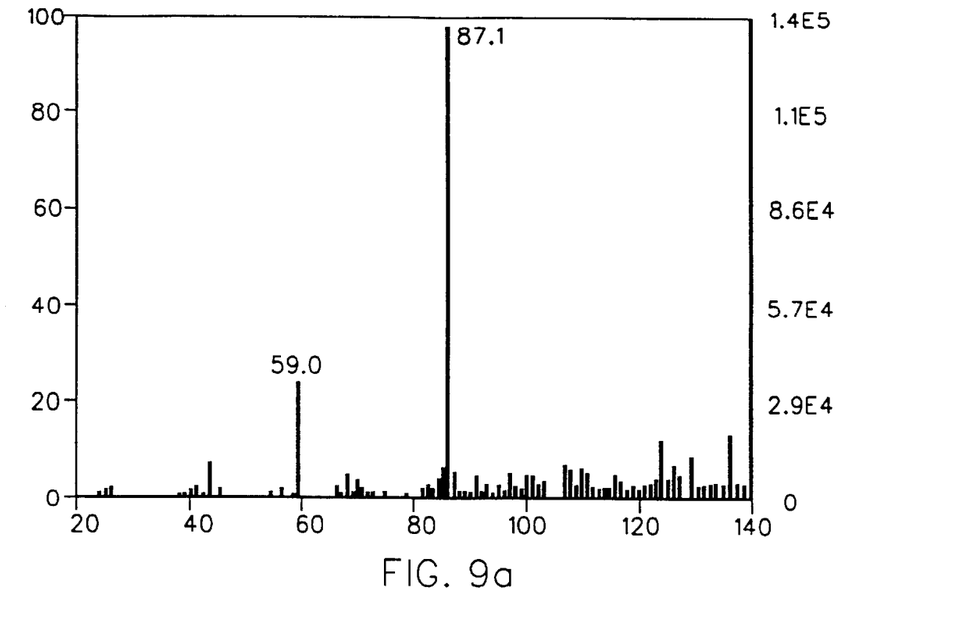
FIG. 9a shows mass spectrometry data at pH 4.5 before extraction of acetic acid in the presence of sodium butyrate.
Figure 9B:
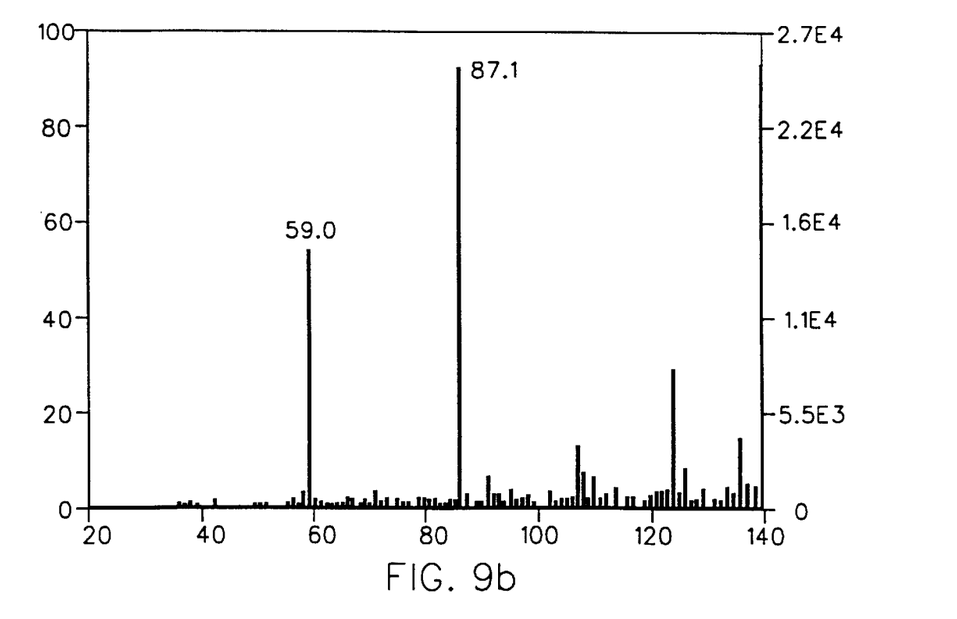
FIG. 9b after extraction of acetic acid in the presence of sodium butyrate.

FIG. 9a shows mass spectrometry data at pH 4.5 before, and FIG. 9b after, extraction of acetic acid in the presence of sodium butyrate. It is apparent from FIGS. 9a and 9b that both acetic and butyrate ions are being extracted. Furthermore, the extraction of salt ions exclusively into the amine phase is ruled out since Alamine 336 does not form complexes with these ions, as described in the previously cited article by Yang et al. (1991).

Therefore, the exchange of butyrate ion with acetate ion should take place in the aqueous phase. From the above results for the extraction of a mixture of acidic solutes, it is clear that the uptake of an individual acid depends upon its chain length and on the nature of all of the salts in solution as well.

For other adsorbents tested, the uptake of acids was quite good, (90%+), as shown in Table 3, although a small amount of alpha-amylase adsorption onto them was observed. Separation of acids and enzymes in a single processing step using sieves and bentonites is not easy because the system now contains two solid adsorbents. Therefore, density difference is a key factor if the simultaneous separation of analytes is undertaken.

TABLE 3

| Material | % uptake |
| --- | --- |
| 3 Å sleve | 94; 97; 99 |
| 10 Å sleve | 92; 95; 98 |
| zeolite | 92; 96; 99 |

Figure 10:
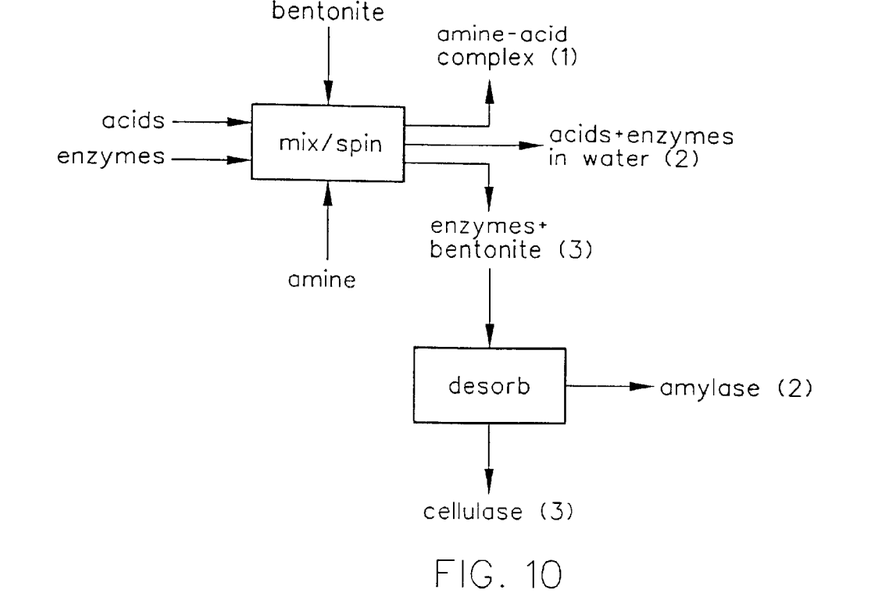
FIG. 10 shows a flow sheet for simultaneous separation where bentonite was used for enzymes uptake and Alamine 336 was used for the extraction of acids.
Figure 11:
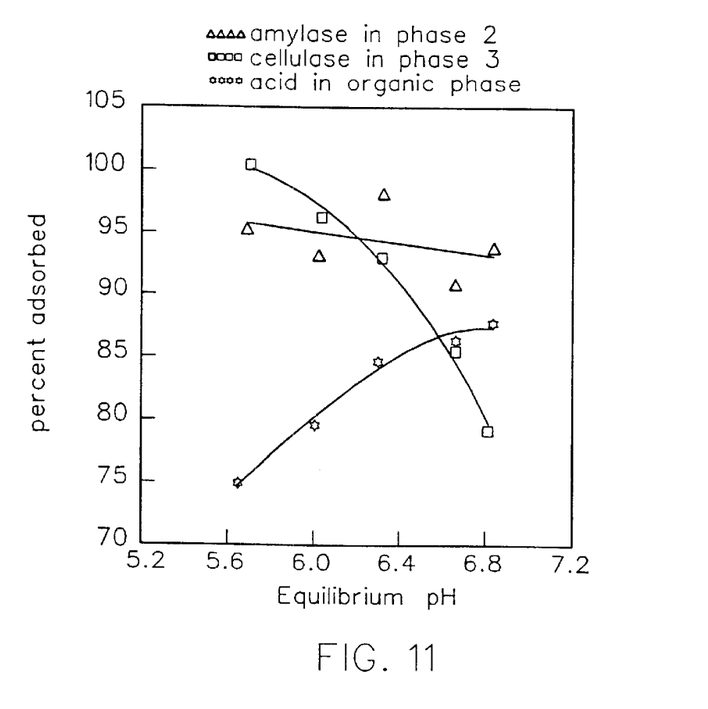
FIG. 11 depicts separation acheived from aqueous solution for alpha-amylase, cellulase and acid.

Additional work was undertaken and for this case the compounds which gave the best results for acids and enzymes were used. Therefore, bentonite was used for enzymes uptake and Alamine 336 was used for the extraction of acids. The corresponding flow sheet for simultaneous separation is shown in FIG. 10. The solution mixture consisting of alpha-amylase, cellulase, acids and bentonite was mixed thoroughly and phases were separated by centrifugation. The corresponding three (3) phases are shown on the right hand side of the flow sheet. The top phase, being lighter, is the amine phase with acids. The bottom phase, being heavier, contains the solid adsorbent with enzymes. The aqueous phase, after equilibration, should contain the unpartitioned solutes. As discussed earlier, the acids extraction is more than 70% complete, whereas for alpha-amylase there is greater than 80% adsorption onto bentonite along with cellulase. The alpha-amylase can be stripped from bentonite into the aqueous phase by shifting pH or by using an eluant with high ionic concentration. In this work, it was desorbed by increasing the solution pH to 8.1. The cellulase showed poor desorptivity and thus was enriched in the adsorbent phase. FIG. 11 depicts results for alpha-amylase, cellulase and acid. Importantly, this process can be made continuous, since the phases are easily separable because of density differences. Further, it is evident that the separation is pH dependent.

It is further noted that low solution pH, though attractive because of high adsorption of the enzyme, affects the amount of acids extracted to the organic phase. Different desorption mechanisms from bentonite for alpha-amylase and cellulase proved useful and a high separation factor between them was achieved. From FIG. 11, it appears that a desirable pH would be close to 6.5, where a good degree of separation of all the solutes will be realized. Moreover, the enzymes are stable in contact with the organic phase which is yet another feature of the process that favors the use of extractant.

In conclusion, it can be stated that the principal advantage of using organic extractant and solid adsorbent to simultaneously separate acids and enzymes is the ease with which these phases can be separated from the aqueous phase, and the ease with which the respective phases can be stripped of solutes, thereby allowing the process to be made continuous. Further, useful analytes like volatile fatty acids and enzymes can be separated utilizing differences in their affinity for various media. At pH's close to neutral conditions the salt ion concentration increases and this affects extraction of acids because of a combination of factors such as chain length, type of salt ion, and hydrophobicity of the acid itself. Thus, salt ions enhance the extraction of acids and also confer stability to the enzyme solution. Further, a process involving adsorbent and extractant can be used to achieve a high degree of separation of acids and enzymes simultaneously. By choosing a system with materials of different densities, the process becomes easy and can be made continuous for large scale operation. Thus, recovery of chemicals from effluent streams is a viable option not only to meet environmental regulations but also as a method for successful management of wastes.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method for producing at least one metal salt of a fatty acid comprising the steps of:
   a. obtaining, from animal rumen, ruminal fluid containing at least one fatty acid selected from the group consisting of:
      valeric;
      acetic;
      propionic; and
      butyric;
   b. adding to said ruminal fluid at least one metal oxide, or combination of metal oxides selected from the group consisting of:
      CaO;
      MgO;
      ZnO;
      CaO+MgO;
      CaO+ZnO; and
      MgO+ZnO;
      such that there is formed at least one metal salt of a fatty acid selected from the group consisting of:
      calcium-valerate;
      calcium acetate;
      calcium-propionate;
      calcium-butyrate;
      zinc-valerate;
      zinc-acetate;
      zinc-propionate;
      zinc-butyrate;
      magnesium-valerate;
      magnesium-acetate;
      magnesium propionate;
      magnesium-butyrate;
      calcium-magnesium-acetate,
      calcium-magnesium-propionate;
      calcium-magnesium-butyrate;
      calcium-zinc-acetate;
      calcium-zinc-propionate;
      calcium-zinc-butyrate;
      magnesium-zinc-acetate;
      magnesium-zinc-propionate; and
      magnesium-zinc-butyrate; and
   c. recovering at least some of said at least one metal salt of a fatty acid.

2. The method of claim 1, which further comprises, after step a, separating-out particulate solids from the ruminal fluid.

3. The method of claim 1, wherein the ruminal fluid further contains alpha-amylase or cellulase, and after step a and prior to step b contacting said ruminal fluid with an adsorbent to adsorb at least some of said alpha-amylase or cellulase from said ruminal fluid.

4. The method of claim 3, wherein the adsorbent is bentonite.

5. The method of claim 3, wherein cellulase is isolated.

6. The method of claim 5, wherein said isolation of said cellulose involves size exclusion chromatography.

7. The method of claim 1 wherein at least some of said at least one metal salt of a fatty acid is applied to an area to be de-iced and functions as a de-icer.

8. A method for isolating at least one enzyme and producing at least one metal salt of a fatty acid comprising the steps of:
   a. obtaining, from animal rumen, ruminal fluid containing at least one fatty acid selected from the group consisting of:
      valeric;
      macetic;
      propionic; and
      butyric;
      and further containing at least one enzyme;
   b. recovering at least some of said at least one enzyme in an undetatured form;
   said method then further comprising the steps of:
   c. adding to said ruminal fluid, from which was recovering at least some of said at least one enzyme in an undenatured form, at least one metal oxide, or combination of metal oxides selected from the group consisting of:
      CaO;
      MgO;
      ZnO;
      CaO+MgO;
      CaO+ZnO; and
      MgO+ZnO;
      such that there is formed at least one metal salt of a fatty acid selected from the group consisting of:
      calcium-valerate;
      calcium-acetate;
      calcium-propionate;
      calcium-butyrate;
      zinc-valerate;
      zinc-acetate;
      zinc-propionate;
      zinc-butyrate;
      magnesium-valarate;
      magnesium-acetate;
      magnesium-propionate;
      magnesium-butyrate;
      calcium-magnesium acetate;
      calcium-magnestum-propionate;
      calcium-magnesium-butyrate;
      calcium-zinc-acetate;
      calcium-zinc-propionate;
      calcium-zinc-butyrate;
      magnesium-zinc-acetate;
      magnesium-zinc-propionate; and
      magnesium-zinc-butyrate; and
   d. recovering at least some of said at least one metal salt of a fatty acid.

9. The method of claim 8 in which recovery of at least some of said at least one enzyme in an undenatured form, is by contact with an adsorbent.

10. the method of claim 9, wherein the adsorbent is bentonite.

11. The method of claim 8 which further comprises, after step a, separating-out particulate solids from the ruminal fluid.

12. The method of claim 8 wherein at least some of said at least one metal salt of a fatty acid is applied to an area to be de-iced and functions as a de-icer.

* * * * *